United States Patent [19]

Nakamura

[11] Patent Number: 4,710,460

[45] Date of Patent: Dec. 1, 1987

[54] DIAGNOSTIC APPLICATIONS OF PHOSPHOFRUCTOKINASE

[76] Inventor: Kunie Nakamura, 3120-10, Kobuchi, Sagamihara-shi, Kanagawa-ken, Japan

[21] Appl. No.: 620,822

[22] Filed: Jun. 15, 1984

[30] Foreign Application Priority Data

Jun. 20, 1983 [JP] Japan ................... 58-109419

[51] Int. Cl.$^4$ .................................. C12Q 1/48
[52] U.S. Cl. ............................. 435/15; 436/64
[58] Field of Search ............. 435/4, 15, 176, 177, 435/182, 194, 805, 810; 436/64

[56] References Cited

U.S. PATENT DOCUMENTS

| | | | |
|---|---|---|---|
| 4,019,961 | 4/1977 | Klose et al. | 435/15 |
| 4,132,600 | 1/1979 | Plotkin et al. | 435/15 |
| 4,323,650 | 4/1982 | Rosevear | 435/176 |
| 4,334,017 | 6/1982 | Plotkin et al. | 435/15 |
| 4,384,045 | 5/1983 | Ho et al. | 435/176 |

FOREIGN PATENT DOCUMENTS

| | | | |
|---|---|---|---|
| 80/02296 | 10/1980 | PCT Int'l Appl. | 435/15 |
| 0635424 | 11/1978 | U.S.S.R. | 435/15 |

OTHER PUBLICATIONS

Chemical Abstracts, vol. 99, No. 21, p. 457, item #173824u, 1983.
Chemical Abstracts, vol. 99, No. 23, p. 40, item #187203c, 1983.
Chemical Abstracts, vol. 102, No. 17, p. 241, item #14509b, 1985.
Chemical Abstracts, vol. 76, No. 13, item #70784b, 1971.
Chemical Abstracts, vol. 96, No. 1, p. 418, item #4517d, 1981.
Chemical Abstracts, vol. 88, No. 19, p. 358, item #134506v, 1978.
Methods of Enzymatic Analysis, edited by Hans Ulrich Bergmeyer, pp. 450–451; 2096–2131, 2nd edition, 1974.
Spectrophotometric Measurement of Hexokinase and Phosphohexokinase Activity, by E. Racker, from the Department of Bacteriology, New York University College of Medicine, New York, pp. 842–855.
Methods in Enzymology, vol. IX, Carbohydrate Metabolism, edited by Willis A. Wood, Michigan State University, Department of Biochemistry, pp. 424–443.

Primary Examiner—Sam Rosen
Assistant Examiner—William J. Herald
Attorney, Agent, or Firm—Lalos & Keegan

[57] ABSTRACT

An enzyme, phosphofructokinase is now found to be applicable to detection of a phosphofructokinase-inhibitor possibly present in supravital serum sample or other body fluid sample as collected from human person. When an abnormally high content or potency of the phosphofructokinase-inhibitor is detected in the body fluid samples such as serum by means of the phosphofructokinase, it indicates probability of presence of malignant neoplasms in the donor for the samples, usefully for diagnosis of the neoplasms.

4 Claims, No Drawings

DIAGNOSTIC APPLICATIONS OF PHOSPHOFRUCTOKINASE

SUMMARY OF THE INVENTION

This invention relates to a reagent for enzymological diagnosis of malignant neoplasms or cancers which is used for the detection of a phosphofructokinase-inhibitor possibly present in a supravital serum sample or other body fluid samples as collected from a human person to be examined, whereby presence of malignant neoplasms or cancers developed in said person can be detected for diagnosis purpose. This invention also relates to a composition of matter having utility in diagnosis of malignant neoplasms or cancers. This invention further relates to a method for diagnosis of malignant neoplasms or cancers in persons by enzymologically detecting a phosphofructokinase-inhibitor possibly present in a supravital serum sample or other body fluid sample, with employing phosphofructokinase as a detecting agent.

BACKGROUND OF THE INVENTION

The present inventor has researched the energy metabolism in the mammals including human and particularly has made extensive study about the enzyme system for glycolysis (known as TCA cycle in biochemistry) which participates in the vital production of energy. In this study, the present inventor has discovered the fact that supravital serum samples as collected from malignant neoplasm-bearing patients always exhibit an abnormally high activity inhibitory to fructose 6-phosphotransferase, namely the phosphofructokinase (sometimes abbreviated as PFK and may also be termed as D-fructose 6-phosphate 1-phosphotransferase)(see a biochemical book "Methods in Enzymology" Vol. IX, "Carbohydrate Metabolism" edited by Willis A. Wood, pages 425–442 (1966), Academic Press, New York). It is known that PFK catalyzes the biochemical reaction of producing fructose 1,6-diphosphate from fructose 6-phosphate. Starting from this discovery, the present inventor has examined how the potency of the phosphofructokinase-inhibiting activity of supravital serum samples or specimens as collected from persons co-relates to the presence of malignant neoplastic cells in the body of said persons (the donors). It has now been found that the serum samples or other body fluid samples as collected from the malignant neoplasm-bearing patients always show a significantly higher phosphofructokinase-inhibiting potency than the serum samples or other body fluid samples as collected from the normal persons who are presumed to be bearing no malignant neoplasms or cancers. The present inventor further has succeeded to separate a substance which may be presumed as a phosphofructokinase-inhibitor, from the serum of malignant neoplasm-bearing patients, and also to examine some properties of such inhibitory substance.

Moreover, it has now been found that the phosphofructokinase-inhibitor or a PFK-inhibitory factor always appears in the body fluids such as serum, pleural effusion, ascites or other fluids of the patients as the malignant neoplastic cells grow in the body of the patients, irrespective of the kinds of the neoplastic cells which have grown within the body of the patients, and that the phosphofructokinase-inhibitor is detectable as an individual hematic substance at a high potency in the blood or serum specimens even at early stages of development of malignant neoplasms in the patients. From this, the present inventor has found that examination of the phosphofructokinase-inhibiting potency or factor of body fluid samples as collected from persons to be examined is useful for early detection of cancer cells, and thus for early diagnosis of malignant neoplasms in potential patients. Thus, it has now been found that phosphofructokinase is useful for diagnosis of malignant neoplasms because of its utility in detecting the phosphofructokinase-inhibitor which is possibly present in the supravital serum samples or other body fluid samples as collected from persons to be examined. This invention is based on the above-mentioned findings.

DETAILED DESCRIPTION OF THE INVENTION

According to a first aspect of this invention, therefore, there is provided a reagent or composition of matter for enzymological diagnosis of malignant neoplasms or cancers by detecting a phosphofructokinase-inhibitor present in a supravital serum sample or other body fluid samples, which comprises an effective amount of a phosphofructokinase as the active ingredient, in association with a carrier for the active ingredient.

According to a second aspect of this invention, there is provided a method of diagnostically detecting malignant neoplasms in a human person, which comprises reacting a phosphofructokinase with a supravital serum sample, a supravital pleural effusion sample or a supravital ascites sample as collected from the person, evaluating how much the enzymatic activity of the phosphofructokinase is inhibited in the reaction with the supravital sample, taking the so evaluated degree of inhibition of the phosphofructokinase activity as an index to estimate whether a phosphofructokinase-inhibitor is present in the supravital sample at such a potency that is abnormally higher than the potencies normally observed with the similar supravital samples as collected from the normal persons who have been confirmed to be bearing no malignant neoplasm, and preliminarily diagnosing the presence of malignant neoplasms in the person when the supravital sample of the donor (the person tested) is estimated to contain the phosphofructokinase-inhibitor at an abnormally high potency.

Phosphofructokinase used according to this invention may preferably be a purified enzyme preparation which has been extracted from various internal organs or tissues and muscle tissue of animals such as rabbits, pigs, cows, horses, chicken and the like by a conventional method, but it may be a crude solution of the enzyme which is available as homogenate of animal's tissues. It may also be a crude enzyme solution or a purified enzyme preparation comprising the enzyme which is produced fermentatively by certain microorganisms. Normally, it is preferred that phosphofructokinase is employed in the form of its aqueous solution containing 0.2 I.U./ml–50 I.U./ml of the enzyme in water, and that the aqueous solution of the enzyme contains further an amount of an enzyme-stabilizer such as ammonium sulfate.

In general, different known assay methods may be adopted to detect and quantitatively determine the phosphofructokinase-inhibitor present in the supravital body fluid samples, with using phosphofructokinase or the reagent of this invention. It is known that the biochemical reaction of producing fructose 6-diphosphate from fructose 6-phosphate in the presence of phosphofructokinase normally requires the presence of adenosine triphosphate (abbreviated as ATP). Therefore, when a supravital serum or similar sample containing the phosphofructokinase-inhibitor is incubated in the presence of phosphofructokinase added thereto, of fructose 6-phosphate initially existing therein or added thereto, and of ATP added thereto, said reaction of producing fructose 1,6-diphosphate takes places in the supravital sample with consuming a proportion of ATP present there, and with involving such a condition that as a principle, the consumption of ATP in the fructose 1,6-diphosphate-producing reaction can be inhibited by a degree which is essentially proportional to the potency of the phosphofructokinase-inhibitor present in said sample. When utilizing these conditions quantitative determination or assay of the phosphofructokinase-inhibitor in the supravital sample can be achieved in an enzymological way.

Thus, it is feasible to make a diagnostic detection and quantitative determination of the phosphofructokinase-inhibitor possibly present in a supravital serum sample or other body fluid samples by reacting known quantities of the reagent of this invention or phosphofructokinase (preferably as aqueous solution), fructose 6-phosphate and ATP with the supravital sample for a predetermined time and at a predetermined temperature and thereafter evaluating directly or indirectly the residual quantity of ATP which is remaining unreacted in the reaction solution without being consumed.

The methods of directly evaluating the residual quantity of ATP include, for example, a method of assaying ATP according to a high performance liquid chromatography (HPLC.).

Further, the methods of indirectly evaluating the residual quantity of ATP include, for example, the undermentioned methods (a) to (f):

(a) Method of Jawrek et al comprising reacting glycerate 3-phosphate with the residual quantity of ATP in the presence of 3-phosphoglycerate kinase (abbreviated as PGK), reacting the resultant glycerate 1,3-$P_2$ (namely, glycerate 1,3-diphosphate), with nicotinamide-adenine dinucleotide, reduced form (abbreviated as NADH), hydrogen cation and glyceraldehyde phosphate dehydrogenase (abbreviated as GAPDH) to produce glyceraldehyde 3-P (namely, glyceraldehyde 3-phosphate) and nicotinamide-adenine dinucleotide cation ($NAD^+$), and then determining colorimetrically the concentration or potency of the $NAD^+$ (see D. Jawrek; W. Gruber & H. U. Bergmeyer "Adenosine 5'-triphosphate, Determination with 3-Phosphoglycerate Kinase, Methods of Enzymatic Analysis" edited by H. U. Bergmeyer, pp. 2097 (1974), published from Verlag Chemie Weinheim, Academic Press Inc., New York & London).

(b) Method of Bergmeyer et al comprising reacting fructose 6-phosphate with the residual quantity of ATP in the presence of phosphofructokinase to produce fructose 1,6-diphosphate and adenosine diphosphate (abbreviated as ADP), reacting the ADP so formed with phosphoenolpyruvic acid (abbreviated as PEP) in the presence of pyruvate kinase (abbreviated as PK) to produce ATP and pyruvic acid, reacting the pyruvic acid so formed with NADH (nicotinamide-adenine dinucleotide, reduced form, (known as co-enzyme)), and hydrogen cation in the presence of lactic acid dehydrogenase to produce L-lactate and $NAD^+$, and then determining colorimetrically the concentration NADH which is remaining unreacted in the last reaction stage (see H. U. Bergmeyer "Fructose 6-phosphate Kinase, Methods of Enzymatic Analysis" edited by H. U. Bergmeyer, pp. 451 (1974), published from Verlag Chemie Weinheim, Academic Press Inc., New York & London).

(c) Method of Lamprecht et al comprising reacting glucose with the residual quantity of ATP in the presence of hexokinase, reacting the resultant glucose 6-phosphate with nicotinamide-adenine dinucleotide phosphate (abbreviated as $NADP^+$) in the presence of glucose 6-phosphate dehydrogenase to produce 6-phosphoglucono-$\delta$-lactone, nicotinamide-adenine dinucleotide phosphate, reduced form (abbreviated as NADPH) and hydrogen cation ($H^+$), and then determining colorimetrically the concentration of the remaining NADPH (see W. Lamprecht & I. Trautschold "Adenosine 5'-triphosphate, Determination with Hexokinase and Glucose 6-phosphate Dehydrogenase, Methods of Enzymatic Analysis" edited by H. U. Bergmeyer, pp. 2101 (1974), published from Verlag Chemie Weinheim, Academic Press Inc., New York & London).

(d) Method of Jawrek et al comprising degrading the residual quantity of ATP to produce ADP, and determining colorimetrically the amount of the ADP so formed, through a determination of the quantity of NADH as consumed (see D. Jawrek; W. Gruber & H. U. Bergmeyer "Adenosine 5'-diphosphate and Adenosine 5'-monophosphate, Methods of Enzymatic Analysis" edited by H. U. Bergmeyer, pp. 2127 (1974), published from Verlag Chemie Weinheim, Academic Press Inc., New York & London).

(e) Method of Rabinowitz et al comprising determining colorimetrically the residual quantity of ATP with using formyltetrahydrofolate synthetase (see J. C. Rabinowitz "Adenosine 5'-triphosphate, Determination with Formyltetrahydrofolate Synthetase, Methods of Enzymatic Analysis" edited by H. U. Bergmeyer, pp. 2110 (1974), published from Verlag Chemie Weinheim, Academic Press Inc., New York & London), and (f) Method of Stehler comprising reacting the residual quantity of ATP with luciferin in the presence of luciferase of firefly origin to produce adenyl luciferin, and determining spectrophotofluorometrically the adenyl luciferin by means of luminescence developed when the adenyl luciferin is reacted with oxygen (see B. L. Stehler "Adenosine 5'-triphosphate and Creatine Phosphate, Determination with Luciferase, Methods of Enzymatic Analysis" edited by H. U. Bergmeyer, pp. 2112 (1974), published from Verlag Chemie Weinheim, Academic Press Inc., New York & London).

Furthermore, when a supravital serum sample or other body fluid sample containing the phosphofructokinase-inhibitor is incubated in the presence of phosphofructokinase added thereto, of ATP added thereto, and of fructose 6-phosphate added thereto, the reaction of producing fructose 1,6-diphosphate takes place as stated hereinbefore, and in this reaction there is also involved and prevails such condition that the formation of the fructose 1,6-diphosphate can be inhibited by a degree which is essentially proportional to the potency of the phosphofructokinase-inhibitor present in said sample. Therefore, it is feasible to make a detection and quantitative determination of the phosphofructokinase-inhibitor present in a supravital serum or similar sample by reacting known quantities of the reagent of this invention or phosphofructokinase (preferably as aqueous solution), ATP and fructose 6-phosphate with the supravital sample for a predetermined period of time and at a predetermined temperature and thereafter evaluating directly or indirectly the quantity of the fructose 1,6-diphosphate as formed in the reaction solution.

The methods of evaluating the quantity of fructose 1,6-diphosphate as formed include, for example, the method of Racker (see E. Racker "Journal of Biological Chemistry" Vol. 167, page 843 (1947)).

According to what the present inventor has confirmed through further experiments, it has been found to be very suitable for diagnosis of malignant neoplasms to carry out the detection and quantitative determination or assay of the phosphofructokinase-inhibitor present in a supravital serum sample or other body fluid sample, according to the method (b) of Bergmeyer et al, thus by having fructose 6-phosphate, fructose 1,6-diphosphate, magnesium sulfate (MgSO$_4$), phosphoenolpyruvic acid (PEP), NADH, pyruvate kinase (PK), lactic acid dehydrogenase (LDH) and ATP ready to use them, mixing these compounds with a mixture of phosphofructokinase (PFK) with a supravital serum, pleural effusion or ascitic fluid sample or the like as collected from the donor (person to be examined), allowing the resultant admixture to undergo the successive enzymatic reactions under controlled conditions, colorimetrically evaluating the residual concentration of the co-enzyme, NADH remaining in the final reaction solution and then calculating therefrom such quantity of NADH which had been consumed in the enzymatic reactions involved.

According to a third aspect of this invention, therefore, there is provided a composition of matter having utility in diagnosis of malignant neoplasms by detection of phosphofructokinase-inhibitor in a supravital serum sample or other body fluid sample, which is essentially consisting of (i) a first solution comprising an aqueous solution of a phosphofructokinase, (ii) a second solution comprising an aqueous solution of adenosine triphosphate, and (iii) a third solution comprising an aqueous solution of a mixture of phosphoenolpyruvic acid, β-nicotinamideadenine dinucleotide (reduced form), pyruvate kinase and lactic acid dehydrogenase in water.

The composition according to the third aspect of this invention is usually stored before its use in such way that the first solution, the second solution and the third solution are placed each in separate packs. Thus, the composition according to the third aspect of this invention is usually provided in a three-part system or a three-pack type of formulation before its use.

The principle for the assaying of the phosphofructokinase-inhibitor present in a supravital serum or other body fluid sample using the diagnostic composition of the third aspect invention is utilizing the following reaction equations:

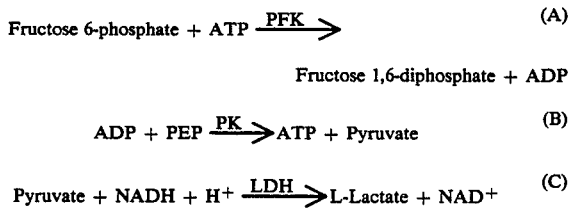

In view of the above equations, when the above enzymatic reactions proceed, it is obvious that if the enzymatic potency of phosphofructokinase (PFK) is inhibited or suppressed by the phosphofructokinase-inhibitor present in the supravital sample to be tested, the consumption of ATP can be suppressed and hence the rate of conversion of ATP into ADP can also be lowered with the consequence that the production of the lactic acid from the pyruvic acid and NADH is suppressed, resulting in a suppressed consumption of NADH. Accordingly, it is evident that the residual quantity of NADH remaining in the final reaction solution which is obtained after a supravital sample containing the phosphofructokinase-inhibitor has completely undergone the successive enzymatic reactions (A), (B), (C) should be higher than the residual quantity of NADH in such reaction solution which is similarly obtained with a supravital sample containing no phosphofructokinase-inhibitor.

The residual quantity of the co-enzyme NADH in the final reaction solution as obtained from the completed enzymatic reaction (C) can, in principle, be determined colorimetrically in such a manner that the value of the light absorbance at 340 nm of the final reaction solution is measured by means of a spectrophotometer and the measured value of the absorbance is compared with such a reference or standard curve (as the control) which has preliminarily been prepared to reveal the co-relationship between the known concentrations of NADH and values of the light absorbance at 340 nm of aqueous solutions containing the known quantities of NADH. While, it is obvious that the grade of the compounds or reagents employed here, the reaction conditions, the conditions of measurement and other parameters involved here are often variable each time, which makes it necessary each time to make troublesome preparation of the reference or standard curve showing the co-relationship between the NADH concentrations and the values of the light absorbance at the different NADH concentrations.

Besides, according to what the present inventor has further found through his experiments, it is possible and more convenient to achieve a "relative" determination of the potency of the phosphofructokinase-inhibitor in the supravital sample, by reacting a phosphofructokinase-inhibitor-containing supravital sample successively with the first solution (the enzyme solution), the second solution and the third solution of the composition of the third aspect invention to allow the series of the aforesaid enzymatic reactions (A), (B) and (C) to proceed, thereby providing such reaction solution where the reaction (C) is going to take place subsequently to the reactions (A) and (B), and at the moment of commencement of the reaction (C), measuring first the value of the light absorbance at 340 nm optimal for NADH of the reaction solution where the reaction (C) just begins to take place (as value a), and after lapse of a predetermined reaction time of e.g. 10 minutes, measuring again the value of the light absorbance at 340 nm of the reaction solution where the reaction (C) has proceeded to some extent (as value b), calculating the value of a reduction in the light absorbance occurring during the lapse of said predetermined reaction time, that is, calculating the numerical difference (a−b) by subtraction of the second measurement value (b) from the first measurement value (a) of the light absorbance, and then comparing the value of reduction in the light absorbance (a−b) between said supravital body fluid sample containing possibly an amount of the phosphofructokinase-inhibitor and such another supravital body fluid sample not containing therein the phosphofructokinase-inhibitor; with taking into account that obviously, the value of reduction in the light absorbance (a−b) should be lower in the PFK-inhibitor-containing supravital sample than in the supravital sample containing no PFK-inhibitor, and hence the value of reduction in the light absorbance (a−b) should be proportional to the quantity of NADH consumed in the enzymatic rection (C) and should be reversely proportional to the initial potency of the phosphofructokinase-inhibitor in the supravital sample. Thus, it is feasible to evaluate the difference in the quantity of the NADH consumed for the predetermined time in the reaction (C) between such PFK-inhibitor-containing supravital sample and such supravital sample not containing the PFK-inhibitor, in comparison. Therefore, it is fesible to relatively evaluate the initial potency of the phosphofructokinase-inhibitor originally present in the supravital sample, with reference to the calculated value of reduction in the light absorbance of the reaction solution. In this way of assaying the phosphofructokinase-inhibitor in supravital samples, the influences of occasional variations in the reaction conditions, the conditions of measurement and other parameters in each measurement time can conveniently be set off.

Thus, the composition according to the third aspect invention may be utilized for diagnostic measurement of the value of reduction in light absorbance at 340 nm of a supravital body fluid sample when reacted with PFK, fructose 6-phosphate, ATP, PEP, PK, NADH and LDH for the purpose of detecting the phosphofructokinase-inhibitor in said sample.

In the diagnostic composition according to the third aspect of this invention, the first solution (i) may preferably contain an effective amount of a phosphofructokinase-stabilizer such as ammonium sulfate and the like added thereto and dissolved therein. Besides, the third solution (iii) for the composition of the third aspect invention may preferably further contain appropriate amounts of Tris-buffer, magnesium sulfate, potassium chloride, fructose 6-phosphate sodium salt, and fructose 1,6-diphosphate, $\beta$-NADH and phosphoenolpyruvic acid dissolved therein, for the purpose of allowing the concerned enzymatic reactions to proceed smoothly. The phosphoenolpyruvic acid present in the third solution may preferably be in the form of its salt e.g. with cyclohexylammonium (CHA salt). Optimal concentrations of these additives may be decided readily through preliminary tests according to the purposes for which the composition is to be used.

According to a fourth aspect of this invention, moreover, there is provided a method of determining the inhibitory potency of a supravital serum sample or other body fluid sample against phosphofructokinase, which comprises the steps of:

(a) adding an aqueous solution of a phosphofructokinase (the first solution) to the supravital serum or other body fluid sample as collected from the donor, (b) then adding to the mixture of the first solution and the supravital sample an aqueous solution of adenosine triphosphate (the second solution), (c) adding to the reaction mixture of the first and second solutions and the supravital sample, within 30 minutes after the addition of the second solution thereto, an aqueous solution of a mixture of phosphoenolpyruvic acid, $\beta$-nicotinamide adenine dinucleotide (reduced form), pyruvate kinase and lactic acid dehydrogenase dissolved in water (the third solution), (d) allowing the resulting admixture to undergo the enzymatic reactions, (e) measuring continuously or successively the light absorbance at 340 nm of the reaction solution where the enzymatic reactions are taking place, in such a way that a first value of the light absorbance at the moment of commencement of the enzymatic reaction caused by the addition of the third solution is measured and then a second value of the light absorbance at 340 nm of said reaction solution after the lapse of a predetermined time is measured.

(f) calculating a numerical difference by subtraction of the second measurement value from the first measurement value, said numerical difference being termed as the value of reduction in the light absorbance, and (g) comparing the so calculated value of reduction in the light absorbance for the supravital sample of said donor with such a reference value (as a control) which is the value of reduction in the light absorbance as similarly measured and calculated with subsupravital serum or other body fluid samples collected from normal persons who are confirmed to be healthy and free from any malignant neoplasms, to detect any abnormality in the aforesaid calculated value of reduction in the light absorbance for the supravital sample of the donor, in comparison with said reference value for the normal persons.

The "reference value" as the control set forth in the above-mentioned step (g) naturally should be such value of reduction in the light absorbance which has been attained by adding and reacting the first solution, the second solution and the third solution to and with the supravital samples of the normal persons just in the same manner as in the above-mentioned steps (a) to (c) and then making the continuous or successive measurement of the light absorbance at 340 nm of the reaction solution in the same manner as in the above-mentioned step (e) before the necessary calculation of the value of reduction in the light absorbance is obtained.

Although the description just above has been made with such a case when the addition of the first solution to the supravital sample is followed by addition of the second solution and then by addition of the third solution, it is also possible to add at first the third solution and then the second solution to the reaction mixture of the first solution with the supravital sample. In the latter case when the sequence of addition of the second and third solutions is thus reversed, the step (e) for measurement of light absorbance of the reaction solution is commenced after the addition of the second solution.

This invention is now illustrated with reference to the following Examples.

EXAMPLE 1

This example shows that a substance which is presumed as the phosphofructokinase-inhibitor separated from the serum as collected from cancer-bearing patient.

Serum (100 ml) was collected from a cancer-bearing patient who suffered from lung cancer, and the serum was mixed with 30 g of ammonium sulfate under stirring, followed by centrifugation at 10,000×G for 30 minutes. The second supernatant so obtained was then mixed with 20 g of ammonium sulfate under well stirring, again followed by centrifugation at 10,000×G for 30 minutes. The deposit as salted-out was removed by filtration and dissolved in water, and the aqueous solution obtained was placed in a dialysis tube made of cellulose film and dialyzed against distilled water with several replacements by fresh distilled water, so that the ammonium sulfate was removed off. The solution so dialyzed was freeze-dried and the resultant powder was taken up at a predetermined dosage into a volume of the serum as collected from a normal person who was free from any malignant neoplasm. The resultant solution was estimated for its activity inhibitory to the phosphofructokinase (PFK). As a result, it was found that the powder fraction which was obtained by salting out the aforesaid second supernatant with totally 50 g/dl of ammonium sulfate was active against PFK. This PFK-inhibitory fraction which was salted out with totally 50 g/dl of ammonium sulfate was again fractionated by gel-filtration on Sephadex G-75 column. Several fractions so obtained were estimated for their PFK-inhibitory activity, and such fraction having molecular weights lower than that of albumin (M.W. less than 20,000, non-dialyzable) was found to have the PFK-inhibitory activity. The active fraction was freeze-dried and dissolved at a potency of 50 mg/ml in a volume of the serum as collected from the normal person who was free from any malignant neoplasm. The resulting solution in the serum (150 μl) was compared with the normal serum for their PFK-inhibitory activity, when it was shown that this solution exhibited its PFK activity reduced to 30% of the PFK activity of the serum of the normal person itself, revealing that said solution surely contained the PFK-inhibitor. When the above-mentioned active fraction (the freeze-dried powder) was dissolved at a dosage of 12.5 mg/ml in the serum of the normal person, the solution so obtained exhibited a PFK activity further much lower than 30% of the PFK activity measured with the serum of the normal person. With much higher dilution of said active fraction with the serum of the normal person, the diluted solution did not show a further decreased PFK activity.

The above procedures were repeated using the pleural effusion (100 ml) or the ascites (100 ml) as collected from the same cancer-bearing patient, or using the serum, the pleural effusion or the ascites as collected from another cancer-bearing persons, when similar results were obtained.

EXAMPLE 2

This example shows that a phosphofructokinase was utilized according to this invention to detect a PFK-inhibitory activity of supravital serum sample as collected from donors for diagnosis of malignant neoplasm in the donors.

The following three formulations were prepared and made ready to use.

| (i) | First Solution: | |
| --- | --- | --- |
| | Aqueous solution of 120 μg/ml of a phosphofructokinase (PFK) of rabbit muscle origin which was dissolved in 3.2 M aqueous ammonium sulfate | 10 μl |
| (ii) | Second Solution: | |
| | Aqueous solution of 10 mg/ml of ATP in distilled water | 0.1 ml |
| (iii) | Third Solution: | |
| | This Third-Solution comprising a mixture of the following solutions: | |
| | Tris-buffer (0.1 M, pH 8.5) | 2.0 ml |
| | Aqueous solution of 10 mg/ml of MgSO₄ and 10 mg/ml of KCl in water | 0.1 ml |
| | Aqueous solution of 10 mg/ml of fructose 6-phosphate sodium salt | 0.2 ml |
| | Aqueous solution of 10 mg/ml of fructose 1,6-diphosphate | 0.1 ml |
| | Aqueous solution of 10 mg/ml of phospho- | 0.1 ml |
| | enolpyruvic acid CHA salt | |
| | Aqueous solution of 5 mg/ml of β-NADH (namely, β-nicotinamide adenine dinucleotide, reduced form) | 0.1 ml |
| | Aqueous solution of 10 mg/ml of pyruvate kinase | 0.003 ml |
| | Aqueous solution of 5 mg/ml of lactic acid dehydrogenase | 0.003 ml |
| | Total | 2.606 ml |

The procedure for examination of the PFK-inhibitory activity of the supravital serum samples was carried out as follows:

(1) The serum sample (0.15 ml) of the donor tested was placed in a 4-ml capacity cell for a spectrophotometer, to which was then added 10 μl of First Solution (the enzyme solution), followed by stirring. The mixture was incubated for 10 minutes at room temperature.

(2) Into the cell containing the incubated mixture was added 0.1 ml of Second Solution (the ATP solution), followed by incubation for 3 minutes at room temperature.

(3) After this, 2.6 ml of Third Solution was added into the reaction solution in the cell.

(4) The cell containing the reaction mixture was immediately set in the spectrophotometer, and the value of the light absorbance at 340 nm of the reaction mixture was measured continuously for 10 minutes. The value of measurement of the light absorbance (b) at the end of 10 minutes of the final reaction (as caused by and after the addition of Third Solution) was subtracted from the value of measurement of the light absorbance (a) at the moment of commencement of the measurement to calculate the numerical difference (a−b), and this numerical difference was taken as the light absorbance reduction value (I).

On the other hand, a number of the supravital serum samples were collected from many normal persons who were estimated as being free from any malignant neoplasm, and these normal serum samples were tested according to the above-mentioned procedures of examination using the First Solution, Second Solution and Third Solution of the same compositions as mentioned above, whereby actual determination was made to estimate how much the light absorbance at 340 nm of the final reaction mixture was reduced for 10 minutes of the final enzymatic reaction occurring after the addition of Third Solution. From this test, it was found that the light absorbance reduction value obtained with the serum samples of the normal persons normally stood within the range of 0.830±0.061 (average±standard deviation). This value was taken as a standard light absorbance reduction value (II).

As will be clear from the foregoing descriptions, by such fact that the light absorbance reduction value (I) actually evaluated with the serum sample of a certain donor is significantly lower than the range of the standard light absorbance reduction value (II) (0.830±0.061) actually evaluated with the serum samples of the normal persons is meant that the residual amount of ATP in the reaction solution derived from the serum sample of the donor tested is abnormally higher after the first enzymatic reaction (A) took place by the addition of First Solution (the PFK solution), and that the residual amount of β-NADH in the final reaction solution derived from the serum sample of the donor tested is abnormally higher after the final enzymatic reaction (C) occurred by the addition of Third Solution comprising β-NADH, revealing conclusively that the serum sample of the donor tested was containing an abnormally high quantity of the phosphofructokinase-inhibitor. This also reveals that the serum of the donor tested was positive in the detection of the phosphofructokinase-inhibitor and that the donor tested was suspicious of the cancer-bearing and needed further close diagnostic examination.

In clinical tests, for instance, three donors A, B and C (adult, one female and two males) were examined according to the above-mentioned procedures for their serum samples. The serum samples of these three donors showed values of 0.840, 0.632 and 0.859, respectively, for the light absorbance reduction value (I) at 340 nm. Thus, the serum sample of the donor B showed a rate of suppression of the phosphofructokinase activity of 24.76% as assumed that the rate of inhibition of the PFK activity was null with the serum samples of the normal persons. When the donor B was further examined by close diagnostic examination, this donor was discovered to be bearing early stomach cancer.

EXAMPLE 3

Supravital serum or other body fluid samples were collected from patients who were confirmed to be bearing malignant neoplasms. These samples were treated with the first solution, the second solution and the third solution of the compositions same as described for First, Second and Third Solutions in Example 2 and according to the examination procedures described in Example 2. These supravital samples so treated were measured for their light absorbance reduction value (at 340 nm) which was actually determined by a spectrophotometer at the end of 10 minutes of the final enzymatic reaction. The results obtained are summarized in the following table.

$$\frac{(I) - (II)}{(II)} \times 100$$

wherein (I) denotes the light absorbance reduction value of the samples of the donors tested and (II) denotes the light absorbance reduction value of the similar samples of the normal persons.

When the figures for "rate (%) of inhibition or promotion in PFK activity" are attached with a "minus" symbol (−), it means that the PFK activity was suppressed by the sample of the donors as compared to the sample of the normal persons.

Besides, in the "Diagnostic estimation" of the above table, the symbol + shows a positive reaction (i.e., suspicious of malignant neoplasm) whereas, the symbol − shows a negative reaction (i.e., not suspicious of malignant neoplasm).

The early gastic cancer patients of Table 1 who were tested in the above examination procedure and estimated as "positive" were then surgically operated on to remove the cancer. One month after the surgical operation, these patients were again examined for the PFK-inhibiting activity of the serum samples as collected from them. The serum samples of the seven patients re-examined were then estimated as "negative", namely as being normal in the second examination of their PFK-inhibitory activity in their serum samples.

Summarizing the results of Table 1 where the values of reduction in the light absorbance owing to the phosphofructokinase-inhibitor present in the serum or pleural effusion samples of the patients suffering from various diseases were evaluated, it can be observed that the diseases which can be detected by the procedure of Example 2 include malignant cancers and diabetes. It is thus revealed that a substance inhibitory to the activity of phosphofructokinase (PFK) is contained in the serum

TABLE 1

| Diseases | Body fluid tested | Found light absorbance reduction value (averaged) | Rate (%) of inhibition or promotion in PFK activity | Diagnostic estimation |
|---|---|---|---|---|
| None (Healthy normal persons) | Serum | 0.840 ± 0.061 | 0 ± 7.32 | (−) |
| Acute hepatitis | Serum | 0.864 ± 0.023 | +2.86 ± 2.62 | (−) |
| Liver cirrhosis | Serum | 0.883 ± 0.091 | +5.12 ± 10.32 | (−) |
| Gastric- and duodenal ulcer | Serum | 0.913 ± 0.108 | +8.81 ± 11.87 | (−) |
| Diabetes | Serum | 0.766 ± 0.066 | −8.81 ± 8.65 | (+) |
| Myoma uteri | Serum | 0.847 ± 0.051 | +0.83 ± 5.98 | (−) |
| Ovarian cystoma | Serum | 0.853 ± 0.022 | +1.55 ± 2.59 | (−) |
| Ovarian cancer | Serum | 0.586 | −30.24 | (+) |
| Early gastric cancer | Serum | 0.627 ± 0.063 | −25.36 ± 10.02 | (+) |
| Progressive gastric cancer | Serum | 0.629 ± 0.077 | −25.12 ± 12.22 | (+) |
| Hepatic cell carcinoma | Serum | 0.667 ± 0.091 | −20.60 ± 13.65 | (+) |
| Esophageal cancer | Serum | 0.636 | −24.29 | (+) |
| Cystic cancer | Serum | 0.724 ± 0.060 | −13.81 ± 8.33 | (+) |
| Pancreatic cancer | Serum | 0.486 ± 0.095 | −42.14 ± 19.50 | (+) |
| Colo-Rectal cancer | Serum | 0.718 ± 0.093 | −14.52 ± 12.90 | (+) |
| Lung cancer | Serum | 0.600 ± 0.034 | −28.57 ± 5.63 | (+) |
| Lung cancer | Pleural effusion | 0.582 ± 0.051 | −30.71 ± 8.75 | (+) |
| Lung tuberculosis | Pleural effusion | 0.887 ± 0.024 | +5.60 ± 2.65 | (−) |
| Malignant melanoma | Serum | 0.480 ± 0.064 | −42.90 ± 13.25 | (+) |
| Malignant lymphoma | Serum | 0.480 ± 0.057 | −42.90 ± 11.82 | (+) |
| Nucleic acids (2.2 μg/3.0 ml) extracted from ascites of gastric cancer-bearing patient | — | 0.613 | −27.02 | (+) |

Note: In Table 1 above, "rate(%) of inhibition or promotion in PFK activity" was calculated by the equation:

or pleural effusion of the patients who are suffering from the malignant neoplasms or diabetes.

As will be clear from the foregoing, the method of examining the PFK-inhibitory activity in the serum samples using the reagent or phosphofructokinase according to this invention is advantageous in that it enables patients of early cancers (particularly those in stomach, pancreas, lung, ovary and others) to be screened out even with using a small volume of the serum as collected from the donors. The invention can provide medical measure according to which patients of early cancer are detected out from a group of persons of 30 or more years old in whom cancers are likely to develop, the patients so detected out are further closely diagnosed and, upon confirmed diagnosis of cancers, therapeutic treatment of the patients is started at an early stage as immediately as possible. The invention also can provide such medical data with which the progress of patients during their therapeutic treatment are observed while judging whether the therapeutic method employed is proper and if the disease relapses.

What I claim is:

1. A method of diagnostically detecting malignant neoplasm from a human body fluid sample which comprises:
   (i) determining the inhibitory potency against phosphofructokinase of a sample by
      (a) adding an aqueous solution of a phosphofructokinase as the first solution to the sample;
      (b) then adding to the mixture of the first solution and the sample an aqueous solution of adenosine triphosphate as the second solution;
      (c) adding to the reaction mixture of the first and second solutions and the sample, within 30 minutes after the addition of the second solution thereto, an aqueous solution of a mixture of phosphoenolpyruvic acid, beta-nicotinamide adenine dinucleotide in reduced form, pyruvate kinase and lactic acid dehydrogenase dissolved in water, as the third solution;
      (d) allowing the resulting admixture to undergo enzymatic reactions;
      (e) measuring by a spectrophotometer the light absorbance at 340 nm of the reaction solution where the enzymatic reactions are taking place, the measurement of the light absorbance at 340 nm being made in such manner that the measurement of a first value of the light absorbance is done at the commencement of the enzymatic reaction caused by the addition of the third solution and then the measurement of a second value of the light absorbance at 340 nm of said reaction solution is done after the lapse of a predetermined time;
      (f) calculating a numerical difference by subtraction of the second value from the first value, said numerical difference being termed as the value of reduction in the light absorbance; and
      (g) comparing the so calculated value of reduction in the light absorbance for the sample with a reference value which is the value of reduction in the light absorbance as similarly measured and calculated with reference samples collected from healthy persons who are confirmed to be free from any malignant neoplasm, to detect any abnormality in the aforesaid calculated value of reduction in the light absorbance for the sample in comparison with said reference value,
   (ii) thereby estimating whether a phosphofructokinase-inhibitor is present in the sample at such a potency that is abnormally higher than the potencies normally observed with the reference samples, and
   (iii) preliminarily diagnosing for the presence of malignant neoplasms when the sample is estimated to contain the phosphofructokinase-inhibitor at an abnormally high potency.

2. A method of diagnostically detecting malignant neoplasm in a human body by determining the inhibitory potency of a human body fluid sample against phosphofructokinase, which comprises the steps of:
   (a) adding an aqueous solution of a phosphofructokinase as the first solution to a sample,
   (b) then adding to the mixture of the first solution and the sample an aqueous solution of adenosine triphosphate as the second solution,
   (c) adding to the reaction mixture of the first and second solutions and the sample, within 30 minutes after the addition of the second solution thereto, an aqueous solution of a mixture of phosphoenolpyruvic acid, beta-nicotinamide adenine dinucleotide in reduced form, pyruvate kinase and lactic acid dehydrogenase dissolved in water, as the third solution,
   (d) allowing the resulting admixture to undergo enzymatic reactions,
   (e) measuring by a spectrophotometer the light absorbance at 340 nm of the reaction solution where the enzymatic reactions are taking place, said measurement of the light absorbance at 340 nm being made in such manner that the measurement of a first value of the light absorbance is done at the commencement of the enzymatic reaction caused by the addition of the third solution and then the measurement of a second value of the light absorbance at 340 nm of said reaction solution is done after the lapse of a predetermined time,
   (f) calculating a numerical difference by subtraction of the second value from the first value, said numerical difference being termed as the value of reduction in the light absorbance, and
   (g) comparing the so calculated value of reduction in the light absorbance for the sample with a reference value as a control which is the value of reduction in the light absorbance as similarly measured and calculated from reference samples free from any malignant neoplasm, to detect any abnormality in the said calculated value of reduction in the light absorbance for the sample, in comparison with said reference value.

3. A method of diagnostically detecting malignant neoplasm in a human comprising:
   reacting a composition containing phosphofructokinase with a sample selected from the group consisting of, a serum sample, a pleural effusion sample and an ascites sample,
   evaluating how much the enzymatic activity of the phosphofructokinase is inhibited in the reaction by the sample,
   taking the so elevated degree of inhibition of the phosphofructokinase activity as an index to estimate whether a phosphofructokinase-inhibitor is present in the sample at such a potency that is abnormally higher than the potencies as are normally observed with reference samples derived from humans with no malignant neoplasm, and
   preliminarily diagnosing the presence of malignant neoplasms in the person when the sample of the person tested is estimated to contain the phosphofructokinase-inhibitor at an abnormally high potency.

4. A method as claimed in claim 3 wherein the composition comprises (i) a first solution comprising an aqueous solution of a phosphofructokinase, (ii) a second solution comprising an aqueous solution of adenosine triphosphate, and (iii) a third solution comprising an aqueous solution of a mixture of phosphoenolpyruvic acid, beta-nicotinamide-adenine dinucleotide (reduced form), pyruvate kinase and lactic acid dehydrogenase in water.

* * * * *